US007763278B2

(12) United States Patent
Cooper et al.

(10) Patent No.: US 7,763,278 B2
(45) Date of Patent: Jul. 27, 2010

(54) NANOPARTICULATE POLYCOSANOL FORMULATIONS AND NOVEL POLYCOSANOL COMBINATIONS

(75) Inventors: Eugene R. Cooper, Berwyn, PA (US); Laura Kline, Harleysville, PA (US); Gary G. Liversidge, West Chester, PA (US); Niels P. Ryde, Malvern, PA (US)

(73) Assignee: Elan Pharma International Ltd., Athlone, County Westmeath (IE)

( * ) Notice: Subject to any disclaimer, the term of this patent is extended or adjusted under 35 U.S.C. 154(b) by 267 days.

(21) Appl. No.: 10/457,811

(22) Filed: Jun. 10, 2003

(65) Prior Publication Data

US 2003/0232796 A1 Dec. 18, 2003

Related U.S. Application Data

(60) Provisional application No. 60/387,463, filed on Jun. 10, 2002.

(51) Int. Cl.
*A61K 9/00* (2006.01)
*A61K 9/10* (2006.01)
*A61K 9/12* (2006.01)
*A61K 9/14* (2006.01)

(52) U.S. Cl. ............... 424/489; 424/498; 424/499; 424/455; 424/45; 424/400

(58) Field of Classification Search ............... 424/489, 424/450, 495, 488, 486, 400, 498, 499, 455, 424/45

See application file for complete search history.

(56) References Cited

U.S. PATENT DOCUMENTS

| | | | |
|---|---|---|---|
| 4,231,938 A | 11/1980 | Monaghan et al. | |
| 4,346,227 A | 8/1982 | Terahara et al. | |
| 4,420,329 A | 12/1983 | Laughlin | |
| 4,444,784 A | 4/1984 | Hoffman et al. | |
| 4,499,289 A | 2/1985 | Baran et al. | |
| 4,647,576 A | 3/1987 | Hoefle et al. | |
| 4,681,893 A | 7/1987 | Roth | |
| 4,686,237 A | 8/1987 | Anderson | |
| 4,783,484 A | 11/1988 | Violante et al. | |
| 4,826,689 A | 5/1989 | Violanto et al. | |
| 4,849,012 A * | 7/1989 | Wilson ............... | 504/353 |
| 4,997,454 A | 3/1991 | Violante et al. | |
| 5,145,684 A * | 9/1992 | Liversidge et al. ......... | 424/489 |
| 5,298,262 A | 3/1994 | Na et al. | |
| 5,302,401 A | 4/1994 | Liversidge et al. | |
| 5,318,767 A | 6/1994 | Liversidge et al. | |
| 5,326,552 A | 7/1994 | Na et al. | |
| 5,328,404 A | 7/1994 | Bacon | |
| 5,336,507 A | 8/1994 | Na et al. | |
| 5,340,564 A | 8/1994 | Illig et al. | |
| 5,346,702 A | 9/1994 | Na et al. | |
| 5,349,957 A | 9/1994 | Yudelson | |
| 5,352,459 A | 10/1994 | Hollister et al. | |
| 5,354,772 A | 10/1994 | Kathawala | |
| 5,399,363 A | 3/1995 | Liversidge et al. | |
| 5,401,492 A | 3/1995 | Kellar et al. | |
| 5,429,824 A | 7/1995 | June | |
| 5,447,710 A | 9/1995 | Na et al. | |
| 5,451,393 A | 9/1995 | Liversidge et al. | |
| 5,466,440 A | 11/1995 | Ruddy et al. | |
| 5,470,583 A | 11/1995 | Na et al. | |
| 5,472,683 A | 12/1995 | Illig | |
| 5,494,683 A | 2/1996 | Liversidge et al. | |
| 5,500,204 A | 3/1996 | Osifo | |
| 5,510,118 A | 4/1996 | Bosch et al. | |
| 5,518,187 A | 5/1996 | Bruno et al. | |
| 5,518,738 A | 5/1996 | Eickhoff et al. | |
| 5,521,218 A | 5/1996 | Osifo | |
| 5,525,328 A | 6/1996 | Bacon et al. | |
| 5,534,270 A | 7/1996 | De Castro | |
| 5,543,133 A | 8/1996 | Swanson et al. | |
| 5,552,160 A | 9/1996 | Liversidge et al. | |
| 5,560,931 A | 10/1996 | Eickhoff et al. | |
| 5,560,932 A | 10/1996 | Bagchi et al. | |
| 5,565,188 A | 10/1996 | Wong et al. | |
| 5,569,448 A | 10/1996 | Wong et al. | |
| 5,571,536 A | 11/1996 | Eickhoff et al. | |
| 5,573,749 A | 11/1996 | Illig | |
| 5,573,750 A | 11/1996 | Singh | |
| 5,573,783 A | 11/1996 | Desieno et al. | |

(Continued)

FOREIGN PATENT DOCUMENTS

EP          0 142 146 A2     5/1985

(Continued)

OTHER PUBLICATIONS

Product data Sheet on Lesstanol® brand of Octacosanol-95% by garuda international, Inc. (revised 2002)- Web link in use since 1998.*

(Continued)

*Primary Examiner*—Mina Haghighatian
(74) *Attorney, Agent, or Firm*—Foley & Lardner LLP

(57) ABSTRACT

The present invention is directed to nanoparticulate compositions comprising one or more polycosanols. The polycosanol particles of the composition have an effective average particle size of less than about 2000 nm. In another aspect of this invention, novel combinations of polycosanols and other cholesterol lowering agents are described and methods of using same are taught.

66 Claims, No Drawings

U.S. PATENT DOCUMENTS

| | | | |
|---|---|---|---|
| 5,580,579 A | 12/1996 | Ruddy et al. | |
| 5,585,108 A | 12/1996 | Ruddy et al. | |
| 5,587,143 A | 12/1996 | Wong | |
| 5,591,456 A | 1/1997 | Franson et al. | |
| 5,593,657 A | 1/1997 | Ruddy et al. | |
| 5,622,938 A | 4/1997 | Wong | |
| 5,628,981 A | 5/1997 | Liversidge et al. | |
| 5,643,552 A | 7/1997 | Illig | |
| 5,662,883 A | 9/1997 | Bagchi et al. | |
| 5,718,388 A | 2/1998 | Czekai et al. | |
| 5,718,919 A | 2/1998 | Ruddy et al. | |
| 5,741,522 A | 4/1998 | Violante et al. | |
| 5,747,001 A | 5/1998 | Wiedmann et al. | |
| 5,776,496 A | 7/1998 | Violante et al. | |
| 5,834,025 A | 11/1998 | De Garavilla et al. | |
| 5,856,316 A * | 1/1999 | Laguna Granja et al. | 514/164 |
| 5,862,999 A | 1/1999 | Czekai et al. | |
| 6,045,829 A | 4/2000 | Liversidge et al. | |
| 6,068,858 A | 5/2000 | Liversidge et al. | |
| 6,153,225 A | 11/2000 | Lee et al. | |
| 6,165,506 A | 12/2000 | Jain et al. | |
| 6,221,400 B1 | 4/2001 | Liversidge et al. | |
| 6,225,354 B1 * | 5/2001 | Perez | 514/724 |
| 6,264,922 B1 | 7/2001 | Wood et al. | |
| 6,267,989 B1 | 7/2001 | Liversidge et al. | |
| 6,270,806 B1 | 8/2001 | Liversidge et al. | |
| 6,316,029 B1 | 11/2001 | Jain et al. | |
| 6,375,986 B1 | 4/2002 | Ryde et al. | |
| 6,428,814 B1 | 8/2002 | Bosch | |
| 6,431,478 B1 | 8/2002 | Reed et al. | |
| 6,432,381 B2 | 8/2002 | Liversidge et al. | |
| 6,579,895 B2 | 6/2003 | Karim et al. | |
| 6,875,443 B2 * | 4/2005 | Dartey et al. | 424/439 |
| 2002/0012675 A1 | 1/2002 | Jain et al. | |

FOREIGN PATENT DOCUMENTS

| | | | |
|---|---|---|---|
| EP | 0 221 025 A1 | 5/1987 | |
| EP | 0 275 796 B2 | 7/1988 | |
| EP | 0 352 885 A2 | 1/1990 | |
| EP | 0 491 226 A1 | 6/1992 | |
| EP | 0 499 299 A2 | 8/1992 | |
| FR | 2 596 393 A1 | 10/1987 | |
| WO | WO 86/03488 A1 | 6/1986 | |
| WO | WO 86/07054 A1 | 12/1986 | |
| WO | WO 90/15593 A1 | 12/1990 | |
| WO | WO 98/07414 A1 | 2/1998 | |
| WO | WO 99/06039 A1 | 2/1999 | |
| WO | WO 00/53164 A1 | 9/2000 | |
| WO | WO 00/78697 A2 | 12/2000 | |
| WO | WO 02/098565 A1 | 12/2002 | |

OTHER PUBLICATIONS

Lindahl et al., "Characterization of Fluids from the Stomach and Proximal Jejunum in Men and Women," *Pharm. Res.*, 14(4): 497-502 (1997).

Patent Abstracts of Japan, vol. 011, No. 315 (C-451), Oct. 14, 1987 & JP 62 099334 A (Nippon Oil & Fats Co Ltd), May 8, 1987, abstract.

* cited by examiner

NANOPARTICULATE POLYCOSANOL FORMULATIONS AND NOVEL POLYCOSANOL COMBINATIONS

FIELD OF THE INVENTION

The present invention relates to nanoparticulate compositions comprising at least one polycosanol and novel polycosanol combinations. The nanoparticulate polycosanol particles preferably have an effective average particle size of less than about 2000 nm. In another aspect, this invention includes novel combinations of polycosanols and other cholesterol lowering agents and methods of using the same.

BACKGROUND OF THE INVENTION

I. Background Regarding Nanoparticulate Active Agent Compositions

Nanoparticulate active agent compositions, first described in U.S. Pat. No. 5,145,684 ("the '684 patent"), are particles consisting of a poorly soluble therapeutic or diagnostic agent having adsorbed onto, or associated with, the surface thereof a non-crosslinked surface stabilizer. Many factors can affect bioavailability including the dosage form and various properties, e.g., dissolution rate of the drug. Poor bioavailability is a significant problem encountered in the development of pharmaceutical compositions, particularly those containing an active ingredient that is poorly soluble in water. By decreasing the particle size of an active agent, the surface area of the composition is increased, thereby generally resulting in an increased bioavailability. The '684 patent does not teach nanoparticulate compositions of polycosanols.

Methods of making nanoparticulate active agent compositions are described in, for example, U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles." None of these patents teach nanoparticulate compositions of polycosanols.

Nanoparticulate active agent compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive Nanoparticulate Compositions Having Cationic Surface Stabilizers;" U.S. Pat. No. 6,431,478 for "Small Scale Mill;" and U.S. Pat. No. 6,432,381 for "Methods for Targeting Drug Delivery to the Upper and/or Lower Gastrointestinal Tract," all of which are specifically incorporated by reference. In addition, U.S. patent application Ser. No. 20020012675 A1, published on Jan. 31, 2002, for "Controlled Release Nanoparticulate Compositions," describes nanoparticulate compositions, and is specifically incorporated by reference. None of these patents teach nanoparticulate compositions of polycosanols.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

II. Background Regarding Polycosanols

Policosanol (polycosanol) produces cholesterol lowering effects within the first 6-8 weeks of use. At a daily dosage of 10 mg taken at night, LDL cholesterol levels typically drop by 20-25% within the first six months of use. At a dosage of 20 mg, LDL levels typically drop by 25-30%. HDL levels typically increase by 15-25% only after two months of use. The combined LDL reduction and HDL increase will produce a significant and dramatic improvement in the LDL to HDL ratio.

Policosanol (polycosanol) produces cholesterol lowering effects within the first 6-8 weeks of use. At a daily dosage of 10 mg taken at night, LDL cholesterol levels typically drop by 20-25% within the first six months of use. At a dosage of 20 mg, LDL levels typically drop by 25-30%. HDL levels typically increase by 15-25% only after two months of use. The combined LDL reduction and HDL increase will produce a significant and dramatic improvement in the LDL to HDL ratio. See http://www.firstratemall.com/cholesterolfreeheart/.

Cholesterol is transported through the bloodstream by special molecules called lipoproteins. There are three main kinds of lipoproteins: high-density lipoprotein (HDL), low-density lipoprotein (LDL), and very low-density lipoprotein (VLDL). LDL carries fats from the liver to the body cells, while HDL carries fat back to the liver. The higher the level of LDL the greater the risk of fat-related illnesses such as atherosclerosis. In contrast, HDL protects against these illnesses because it removes fats from circulation and puts them back into storage in the liver.

The fatty acids in policosanol are primarily 1-Octacosanol, 1-Triacontanol, 1-Tetracosanol, and 1-Hexacosanol. Typical usage levels range from 500-10,000 micrograms per serving/dose. Typical commercially available commercial compositions are 90% minimum fatty alcohols of (a) 1-Tetracosanol: 0-10%; (b) 1-Hexacosanol: 2-15%; (c) 1-Heptacosanol: 0-0.5%; (d) 1-Octacosanol: 55-70%; (e) 1-Nonacosanol: 0-10%; (f) 1-Triacontanol: 5-20%; (g) 1-Dotriacontanol: 0.1-10%; and (h) 1-Tetratriacontanol: 0.1-10%.

It would be desirable to provide stable, dispersible polycosanol particles, up to about the 2000 nm size range, which can be readily prepared and formulated in pharmaceutically useful and more convenient, palatable forms for consumption. The present invention satisfies these needs.

SUMMARY OF THE INVENTION

The present invention relates to nanoparticulate active agent compositions comprising at least one polycosanol and novel polycosanol combinations. The compositions preferably comprise at least one polycosanol and at least one surface stabilizer adsorbed on or associated with the surface of the one or more polycosanol particles. The nanoparticulate polycosanol particles preferably have an effective average particle size of less than about 2000 nm.

Another aspect of the invention is directed to pharmaceutical compositions comprising a nanoparticulate polycosanol composition of the invention. The pharmaceutical compositions preferably comprise at least one polycosanol, at least one surface stabilizer, and at least one pharmaceutically acceptable carrier, as well as any desired excipients known to those in the art and formulated into the dosage form desired.

In another aspect of this invention, novel combinations of polycosanols and at least one other cholesterol lowering agent are described and methods of using the same are taught.

Another aspect of the invention is directed to a nanoparticulate polycosanol composition having improved pharmacokinetic profiles as compared to conventional microcrystalline polycosanol formulations, such as improved $T_{max}$, $C_{max}$, and/or AUC parameters.

One embodiment of the invention encompasses a polycosanol composition, wherein the pharmacokinetic profile of the polycosanol is not affected by the fed or fasted state of a subject ingesting the composition, preferably as defined by $C_{max}$ and AUC guidelines given by the U.S. Food and Drug Administration and/or the corresponding European regulatory agency (EMEA).

In yet another embodiment, the invention encompasses a polycosanol composition of the invention, wherein administration of the composition to a subject in a fasted state is bioequivalent to administration of the composition to a subject in a fed state, in particular as defined by $C_{max}$ and AUC guidelines given by the U.S. Food and Drug Administration and the corresponding European regulatory agency (EMEA).

Other embodiments of the invention include, but are not limited to, nanoparticulate polycosanol compositions which, as compared to conventional non-nanoparticulate formulations of the same polycosanol, preferably have one or more of the following properties: (1) smaller tablet or other solid dosage form size; (2) smaller doses of drug required to obtain the same pharmacological effect; (3) increased bioavailability; (4) an increased rate of dissolution for the nanoparticulate polycosanol compositions; and (6) bioadhesive polycosanol compositions.

This invention further discloses a method of making a nanoparticulate polycosanol composition according to the invention. Such method comprises contacting at least one polycosanol with at least one surface stabilizer for a time and under conditions sufficient to provide a nanoparticulate polycosanol composition. The one or more surface stabilizers can be contacted with the polycosanol before, preferably during, or after size reduction of the polycosanol.

The present invention is also directed to methods of treatment using the nanoparticulate polycosanol compositions of the invention for conditions such as hypercholesterolemia, hypertriglyceridemia, coronary heart disease, and peripheral vascular disease (including symptomatic carotid artery disease). In one aspect, the compositions of the invention can be used as adjunctive therapy to diet for the reduction of LDL-C, total-C, triglycerides, and Apo B in adult patients with primary hypercholesterolemia or mixed dyslipidemia (Fredrickson Types IIa and IIb). In another aspect, the compositions can be used as adjunctive therapy to diet for treatment of adult patients with hypertriglyceridemia (Fredrickson Types IV and V hyperlipidemia). Markedly elevated levels of serum tryglycerides (e.g., >2000 mg/dL) may increase the risk of developing pancreatitis. Other diseases that may be directly or indirectly associated with elevated, uncontrolled cholesterol metabolism, e.g., restenosis and Alzheimer's disease, may also be treated with the compositions of this invention. Other methods of treatment using the nanoparticulate polycosanol compositions of the present invention are known to those of skill in the art.

Such methods comprise administering to a subject a therapeutically effective amount of a nanoparticulate polycosanol pharmaceutical composition according to the invention.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention relates to nanoparticulate active agent compositions comprising at least one polycosanol and novel polycosanol combinations. The compositions preferably comprise at least one polycosanol and at least one surface stabilizer adsorbed on or associated with the surface of the polycosanol particles. The nanoparticulate polycosanol particles preferably have an effective average particle size of less than about 2000 nm.

As taught in the '684 patent, not every combination of surface stabilizer and active agent will result in a stable nanoparticulate composition. It was surprisingly discovered that stable nanoparticulate polycosanol compositions can be made.

A need exists for safer and higher potency polycosanols. Compositions of nanoparticulate polycosanols decrease the amount of drug needed and this, in turn, decreases adverse side effects while providing maximum dose response. Additionally, a longer plasma half-life is believed to be associated with nanoparticulate polycosanol compositions of the invention. Moreover, increasing the duration of effect of the polycosanol compositions is expected to result in even lower serum cholesterol levels, with a further reduction in dose expected.

In general, the rate of dissolution of a particulate drug can increase with increasing surface area, e.g., decreasing particle size. Consequently, methods of making finely divided drugs have been studied and efforts have been made to control the size and size range of drug particles in pharmaceutical compositions. However, nanoparticulate active agent formulations suitable for administration as a pharmaceutical require formulation of the active ingredient into a colloidal dispersion exhibiting the acceptable nanoparticle size range and the stability to maintain such size range and not agglomerate. Merely increasing surface area by decreasing particle size does not assure success. Further challenges include forming solid dose forms redispersible into the nanoparticle form upon administration to the patient to maintain the benefit of the nanoparticle polycosanol over the traditional dosage form.

Advantages of the nanoparticulate polycosanol compositions of the invention as compared to conventional non-nanoparticulate formulations of the same polycosanol preferably include, but are not limited to: (1) smaller tablet or other solid dosage form size; (2) smaller doses of drug required to obtain the same pharmacological effect; (3) increased bioavailability; (4) substantially similar pharmacokinetic profiles of the nanoparticulate polycosanol compositions when administered in the fed versus the fasted state; (5) improved pharmacokinetic profiles; (6) bioequivalency of the nanoparticulate polycosanol compositions when administered in the fed versus the fasted state; (7) an increased rate of dissolution for the nanoparticulate polycosanol compositions; (8) bioadhesive polycosanol compositions; and (9) the nanoparticulate polycosanol compositions can be used in conjunction with other active agents.

The present invention also includes nanoparticulate polycosanol compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral administration in solid, liquid, or aerosol form, vaginal, nasal, rectal, ocular, local (powders, ointments or drops), buccal, intracisternal, intraperitoneal, or topical administration, and the like.

A preferred dosage form of the invention is a solid dosage form, although any pharmaceutically acceptable dosage form can be utilized. Exemplary solid dosage forms include, but are not limited to, tablets, capsules, sachets, lozenges, powders, pills, or granules. The solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof. A solid dose tablet formulation is preferred.

The preferred method by which the composition of the present invention is used to reduce cholesterol absorption includes the step of mixing the composition with foods and beverages and mixing. The novel food additive is also effective as an additive in margarine, cooking oils or shortening and preferably fruit and vegetable juices preferably orange or tomato juice for the purpose of reducing serum cholesterol in humans who ingest food products made with the novel composition of this invention.

The present invention is described herein using several definitions, as set forth below and throughout the application.

"About" will be understood by persons of ordinary skill in the art and will vary to some extent on the context in which the term is used. If there are uses of the term which are not clear to persons of ordinary skill in the art given the context in which it is used, "about" will mean up to plus or minus 10% of the particular term.

"Conventional" or "non-nanoparticulate active agent" shall mean an active agent which is solubilized or which has an effective average particle size of greater than about 2 microns.

"Poorly water soluble drugs" as used herein means those having a solubility of less than about 30 mg/ml, preferably less than about 20 mg/ml, preferably less than about 10 mg/ml, or preferably less than about 1 mg/ml. Such drugs tend to be eliminated from the gastrointestinal tract before being absorbed into the circulation. Moreover, poorly water soluble drugs tend to be unsafe for intravenous administration techniques, which are used primarily in conjunction with highly water soluble drug substances.

As used herein with reference to stable polycosanol particles, "stable" includes, but is not limited to, one or more of the following parameters: (1) that the polycosanol particles do not appreciably flocculate or agglomerate due to interparticle attractive forces, or otherwise significantly increase in particle size over time; (2) that the physical structure of the polycosanol particles is not altered over time, such as by conversion from an amorphous phase to crystalline phase; (3) that the polycosanol particles are chemically stable; and/or (4) where the polycosanol has not been subject to a heating step at or above the melting point of the polycosanol in the preparation of the nanoparticles of the invention.

"Therapeutically effective amount" as used herein with respect to a drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a 'therapeutically effective amount' by those skilled in the art. It is to be further understood that drug dosages are, in particular instances, measured as oral dosages, or with reference to drug levels as measured in blood.

I. Preferred Characteristics of the Polycosanol Compositions of the Invention

A. Increased Bioavailability and Lower Dosages

The polycosanol compositions of the invention preferably exhibit increased bioavailability, at the same dose of the same polycosanol, require smaller doses, and show longer plasma half-life as compared to prior conventional polycosanol formulations.

In one aspect of the invention, pharmaceutical polycosanol compositions have enhanced bioavailability such that the polycosanol dosage can be reduced, resulting in a decrease in toxicity associated with such polycosanols. It has been surprisingly found in the present invention that stable compositions of nanoparticulate polycosanols can be formed that permit therapeutic levels at desirably lower dosage.

Greater bioavailability of the polycosanol compositions of the invention can enable a smaller solid dosage size. This is particularly significant for patient populations such as the elderly, juvenile, and infant.

B. Improved Pharmacokinetic Profiles

The invention also preferably provides polycosanol compositions having a desirable pharmacokinetic profile when administered to mammalian subjects. The desirable pharmacokinetic profile of the polycosanol compositions preferably includes, but is not limited to: (1) that the $T_{max}$ of a polycosanol when assayed in the plasma of a mammalian subject following administration is preferably less than the $T_{max}$ for a conventional, non-nanoparticulate form of the same polycosanol, administered at the same dosage; (2) that the $C_{max}$ of a polycosanol when assayed in the plasma of a mammalian subject following administration is preferably greater than the $C_{max}$ for a conventional, non-nanoparticulate form of the same polycosanol, administered at the same dosage; and/or (3) that the AUC of a polycosanol when assayed in the plasma of a mammalian subject following administration, is preferably greater than the AUC for a conventional, non-nanoparticulate form of the same polycosanol, administered at the same dosage.

The desirable pharmacokinetic profile, as used herein, is the pharmacokinetic profile measured after the initial dose of a polycosanol. The compositions can be formulated in any way as described below and as known to those of skill in the art.

A preferred polycosanol composition of the invention exhibits in comparative pharmacokinetic testing with a non-nanoparticulate formulation of the same polycosanol, administered at the same dosage, a $T_{max}$ not greater than about 90%, not greater than about 80%, not greater than about 70%, not greater than about 60%, not greater than about 50%, not greater than about 30%, not greater than about 25%, not greater than about 20%, not greater than about 15%, or not greater than about 10% of the $T_{max}$, exhibited by the non-nanoparticulate formulation of the same polycosanol.

A preferred polycosanol and composition of the invention exhibits in comparative pharmacokinetic testing with a non-nanoparticulate formulation of the same polycosanol, administered at the same dosage, a $C_{max}$ which is at least about 10%, at least about 20%, at least about 30%, at least about 40%, at least about 50%, at least about 60%, at least about 70%, at least about 80%, at least about 90%, or at least about 100% greater than the $C_{max}$ exhibited by the non-nanoparticulate formulation of the same polycosanol.

A preferred polycosanol composition of the invention exhibits in comparative pharmacokinetic testing with a non-nanoparticulate formulation of the same polycosanol, administered at the same dosage, an AUC which is at least about 10%, at least about 20%, at least about 30%, at least about 40%, at least about 50%, at least about 60%, at least about 70%, at least about 80%, at least about 90%, or at least about 100% greater than the AUC exhibited by the non-nanoparticulate formulation of the same polycosanol.

Any formulation giving the desired pharmacokinetic profile is suitable for administration according to the present methods. Exemplary types of formulations giving such profiles are liquid dispersions, gels, aerosols, ointments, creams, solid dose forms, etc. of a nanoparticulate polycosanol.

C. The Pharmacokinetic Profiles of the Polycosanol Compositions of the Invention are not Affected by the Fed or Fasted State of the Subject Ingesting the Compositions The invention encompasses polycosanol compositions wherein the pharmacokinetic profile of the polycosanol is preferably not substantially affected by the fed or fasted state of a subject ingesting the composition, when administered to a human. This means that there is no substantial difference in the quantity of drug absorbed or the rate of drug absorption when the nanoparticulate polycosanol compositions are administered in the fed versus the fasted state.

The invention also encompasses a polycosanol composition in which administration of the composition to a subject in a fasted state is bioequivalent to administration of the composition to a subject in a fed state. "Bioequivalency" is preferably established by a 90% Confidence Interval (CI) of between 0.80 and 1.25 for both $C_{max}$ and AUC under U.S. Food and Drug Administration regulatory guidelines, or a 90% CI for AUC of between 0.80 to 1.25, and a 90% CI for $C_{max}$ of between 0.70 to 1.43, under the European EMEA regulatory guidelines ($T_{max}$ is not relevant for bioequivalency determinations under USFDA and EMEA regulatory guidelines).

Benefits of a dosage form which substantially eliminates the effect of food include an increase in subject convenience, thereby increasing subject compliance, as the subject does not need to ensure that they are taking a dose either with or without food. This is significant, as with poor subject compliance an increase in the medical condition for which the drug is being prescribed may be observed.

The difference in absorption of the polycosanol compositions of the invention, when administered in the fed versus the fasted state, preferably is less than about 100%, less than about 90%, less than about 80%, less than about 70%, less than about 60%, less than about 50%, less than about 40%, less than about 30%, less than about 25%, less than about 20%, less than about 15%, less than about 10%, less than about 5%, or less than about 3%.

D. Dissolution Profiles of the Polycosanol Compositions of the Invention

The polycosanol compositions of the invention preferably have unexpectedly dramatic dissolution profiles. Rapid dissolution of an administered active agent is preferable, as faster dissolution generally leads to faster onset of action and greater bioavailability. To improve the dissolution profile and bioavailability of polycosanols it would be useful to increase the drug's dissolution so that it could attain a level close to 100%.

The polycosanol compositions of the invention preferably have a dissolution profile in which within about 5 minutes at least about 20% of the composition is dissolved. In other embodiments of the invention, at least about 30% or about 40% of the polycosanol composition is dissolved within about 5 minutes. In yet other embodiments of the invention, preferably at least about 40%, about 50%, about 60%, about 70%, or about 80% of the polycosanol composition is dissolved within about 10 minutes. Finally, in another embodiment of the invention, preferably at least about 70%, about 80%, about 90%, or about 100% of the polycosanol composition is dissolved within about 20 minutes.

Dissolution is preferably measured in a medium which is discriminating. Such a dissolution medium will produce two very different dissolution curves for two products having very different dissolution profiles in gastric juices; i.e., the dissolution medium is predictive of in vivo dissolution of a composition. An exemplary dissolution medium is an aqueous medium containing the surfactant sodium lauryl sulfate at 0.025 M. Determination of the amount dissolved can be carried out by spectrophotometry. The rotating blade method (European Pharmacopoeia) can be used to measure dissolution.

E. Redispersibility Profiles of the Polycosanol Compositions of the Invention

An additional feature of the polycosanol compositions of the invention is that the compositions preferably redisperse such that the effective average particle size of the redispersed polycosanol particles is less than about 2 microns. This is significant, as if upon administration the nanoparticulate polycosanol compositions of the invention did not redisperse to a substantially nanoparticulate particle size, then the dosage form may lose the benefits afforded by formulating the polycosanol into a nanoparticulate particle size.

This is because nanoparticulate active agent compositions benefit from the small particle size of the active agent; if the active agent does not redisperse into the small particle sizes upon administration, then "clumps" or agglomerated active agent particles are formed, owing to the extremely high surface free energy of the nanoparticulate system and the thermodynamic driving force to achieve an overall reduction in free energy. With the formation of such agglomerated particles, the bioavailability of the dosage form may fall well below that observed with the liquid dispersion form of the nanoparticulate active agent.

Moreover, the nanoparticulate polycosanol compositions of the invention preferably exhibit dramatic redispersion of the nanoparticulate polycosanol particles upon administration to a mammal, such as a human or animal, as demonstrated by reconstitution/redispersion in a biorelevant aqueous media such that the effective average particle size of the redispersed polycosanol particles is less than about 2 microns. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1 M while fasted state intestinal fluid has an ionic strength of about 0.14. See e.g., Lindahl et al., "Characterization of Fluids from the Stomach and Proximal Jejunum in Men and Women," *Pharm. Res.*, 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 M, and NaCl solutions, ranging in concentration from about 0.001 to about 0.1 M, and mixtures thereof. For example, electrolyte solutions can be, but are not limited to, about 0.1 M HCl or less, about 0.01 M HCl or less, about 0.001 M HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 M HCl, 0.01 M HCl, and 0.1 M HCl correspond to pH 3, pH 2, and pH 1, respectively. Thus, a 0.01 M HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+ sodium, potassium and calcium salts of chloride.

In other embodiments of the invention, the redispersed polycosanol particles of the invention (redispersed in an aqueous, biorelevant, or any other suitable media) have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than about 2000 nm" it is meant that at least 50% of the polycosanol particles have a particle size of less than the effective average, by weight, i.e., less than about 2000 nm, 1900 nm, 1800 nm, etc., when measured by the above-noted techniques. Preferably, at least about 70%, about 90%, about 95%, or about 99% of the polycosanol particles have a particle size of less than the effective average, i.e., less than about 2000 nm, 1900 nm, 1800 nm, 1700 nm, etc.

Redispersibility can be tested using any suitable means known in the art. See e.g., the example sections of U.S. Pat. No. 6,375,986 for "Solid Dose Nanoparticulate Compositions Comprising a Synergistic Combination of a Polymeric Surface Stabilizer and Dioctyl Sodium Sulfosuccinate."

F. Bioadhesive polycosanol Compositions

Bioadhesive polycosanol compositions of the invention comprise at least one cationic surface stabilizer, which are described in more detail below. Bioadhesive formulations of polycosanols exhibit exceptional bioadhesion to biological surfaces, such as mucous. The term bioadhesion refers to any attractive interaction between two biological surfaces or between a biological and a synthetic surface. In the case of bioadhesive nanoparticulate polycosanol compositions, the term bioadhesion is used to describe the adhesion between the nanoparticulate polycosanol compositions and a biological substrate (i.e. gastrointestinal mucin, lung tissue, nasal mucosa, etc.). See e.g., U.S. Pat. No. 6,428,814 for "Bioadhesive Nanoparticulate Compositions Having Cationic Surface Stabilizers," which is specifically incorporated by reference.

There are basically two mechanisms which may be responsible for the bioadhesion phenomena: mechanical or physical interactions and chemical interactions. The first of these, mechanical or physical mechanisms, involves the physical interlocking or interpenetration between a bioadhesive entity and the receptor tissue, resulting from a good wetting of the bioadhesive surface, swelling of the bioadhesive polymer, penetration of the bioadhesive entity into a crevice of the tissue surface, or interpenetration of bioadhesive composition chains with those of the mucous or other such related tissues. The second possible mechanism of bioadhesion incorporates forces such as ionic attraction, dipolar forces, van der Waals interactions, and hydrogen bonds. It is this form of bioadhesion which is primarily responsible for the bioadhesive properties of the nanoparticulate polycosanol compositions of the invention. However, physical and mechanical interactions may also play a secondary role in the bioadhesion of such nanoparticulate compositions.

The bioadhesive polycosanol compositions of the invention are useful in any situation in which it is desirable to apply the compositions to a biological surface. The bioadhesive polycosanol compositions coat the targeted surface in a continuous and uniform film which is invisible to the naked human eye.

A bioadhesive polycosanol composition slows the transit of the composition, and some polycosanol particles would also most likely adhere to tissue other than the mucous cells and therefore give a prolonged exposure to the polycosanol, thereby increasing absorption and the bioavailability of the administered dosage.

G. Polycosanol Compositions Used in Conjunction with Other Active Agents

The polycosanol compositions of the invention can additionally comprise one or more non-polycosanol compounds useful: (1) in treating conditions such as dyslipidemia, hyperlipidemia, hypercholesterolemia, cardiovascular disorders, hypertriglyceridemia, coronary heart disease, and peripheral vascular disease (including symptomatic carotid artery disease), or related conditions; (2) as adjunctive therapy to diet for the reduction of LDL-C, total-C, triglycerides, and/or Apo B in adult patients with primary hypercholesterolemia or mixed dyslipidemia (Fredrickson Types IIa and IIb); (3) as adjunctive therapy to diet for treatment of adult patients with hypertriglyceridemia (Fredrickson Types IV and V hyperlipidemia); (4) in treating pancreatitis; (5) in treating restenosis; and/or (6) in treating Alzheimer's disease.

Exemplary non-polycosanol compositions useful in the invention include, but are not limited to, cholesterol lowering agents, alkanoyl L-carnitines, antihypertensives, statins, stanols, and/or sterols.

Useful cholesterol lowering agents are well known to those of skill in the art and include, but are not limited to, ACE inhibitors, nicotinic acid, niacin, bile acid sequestrants, fibrates, vitamins, fatty acid derivatives such as fish oil, long chain plant extract alcohols such as policosinol, ezetimibe, and celluloses.

Useful alkanoyl L-carnitines include, but are not limited to, acetyl L-carnitine, propionyl L-carnitine, butyryl L-carnitine, valeryl L-carnitine, and isovaleryl L-carnitine, or a pharmacologically acceptable salt thereof.

Useful antihypertensives include, but are not limited to diuretics ("water pills", beta blockers, alpha blockers, alpha-beta blockers, sympathetic nerve inhibitors, angiotensin converting enzyme (ACE) inhibitors, calcium channel blockers, angiotensin receptor blockers (formal medical name angiotensin-2-receptor antagonists, known as "sartans" for short).

Useful statins include, but are not limited to, atorvastatin (Lipitor® brand) (U.S. Pat. No. 4,681,893) and other 6-[2-(substituted-pyrrol-1-yl)alkyl]pyran-2-ones and derivatives as disclosed in U.S. Pat. No. 4,647,576); fluvastatin (Lescol® brand) (U.S. Pat. No. 5,354,772); lovastatin (U.S. Pat. No. 4,231,938); pravastatin (U.S. Pat. No. 4,346,227); simvastatin (U.S. Pat. No. 4,444,784); velostatin; fluindostatin (Sandoz XU-62-320); pyrazole analogs of mevalonolactone derivatives, as disclosed in PCT application WO 86/03488; rivastatin and other pyridyldihydroxyheptenoic acids, as disclosed in European Patent 491226A; Searle's SC-45355 (a 3-substituted pentanedioic acid derivative); dichloroacetate; imidazole analogs of mevalonolactone, as disclosed in PCT application WO 86/07054; 3-carboxy-2-hydroxy-propane—phosphonic acid derivatives, as disclosed in French Patent No. 2,596,393; 2,3-di-substituted pyrrole, furan, and thiophene derivatives, as disclosed in European patent application No. 0221025; naphthyl analogs of mevalonolactone, as disclosed in U.S. Pat. No. 4,686,237; octahydronaphthalenes, such as those disclosed in U.S. Pat. No. 4,499,289; keto analogs of mevinolin (lovastatin), as disclosed in European Patent Application No. 0,142,146 A2; phosphinic acid compounds; as well as other HMG CoA reductase inhibitors.

Useful sterols and/or stanols include, but are not limited to, plant sterols, plant sterol esters, fish oil, sitosterol, sitostanol, phytosterol, campestanol, stigmasterol, coprostanol, cholestanol, and beta-sitosterol.

The term "stanol" is well known to those skilled in the art and generally refers to compounds having a saturated perhydrocyclopentanophenanthrene ring system and having one or more OH substituents. "Stanols" as used herein mean plant stanol esters, a food ingredient that can help reduce LDL cholesterol. Plant stanols are derived from naturally occurring substances in plants by techniques known to those in the art.

Such additional compounds can have a conventional non-nanoparticulate particle size, i.e., an effective average particle size greater than about 2 microns, or such additional compounds can be formulated into a nanoparticulate particle size, i.e., an effective average particle size of less than about 2 microns. If such one or more non-polycosanol compounds have a nanoparticulate particle size, then preferably such non-polycosanol compounds are poorly soluble in at least one liquid media (poorly soluble as defined in the "Definitions" section, above), and have at least one surface stabilizer adsorbed on or associated with the surface of the non-polycosanol compound. The one or more surface stabilizers utilized in the composition of the non-polycosanol compound can be the same as or different from the one or more surface stabilizers utilized in the polycosanol composition. A description of surface stabilizers useful in the invention is provided below.

II. Compositions

The present invention is directed to nanoparticulate active agent compositions comprising at least one polycosanol, and novel polycosanol combinations. The compositions preferably comprise: (1) at least one polycosanol or a salt thereof; and (2) at least one surface stabilizer adsorbed on, or associated with, the surface of the polycosanol. The nanoparticulate polycosanol particles preferably have an effective average particle size of less than about 2000 nm. In another aspect of this invention, novel combinations of polycosanols and other cholesterol lowering agents are described and methods of using the same are taught.

The present invention also includes nanoparticulate polycosanol compositions together with one or more non-toxic physiologically acceptable carriers, adjuvants, or vehicles, collectively referred to as carriers. The compositions can be formulated for various routes of administration including but not limited to, oral, rectal, ocular, and parenteral injection (e.g., intravenous, intramuscular, or subcutaneous), oral administration in solid (the preferred route), liquid, or aerosol form, vaginal, nasal, rectal, ocular, local (e.g., in powder, ointment or drop form), buccal, intracisternal, intraperitoneal, or topical administration, and the like.

A. Polycosanol Particles

Useful polycosanols include, but are not limited to, triacontanol, hexacontanol, ecocosanol, hexacosanol, tetracosanol, dotriacontanol, tetracontanol, or natural products or extracts from natural products containing such compounds.

Policosanol (polycosanol) is a complex mixture of concentrated n-alkyl alcohols derived from, for example, sugar cane and the wax of honey bees. Polycosanols are extracted by known methods. These active substances act to lower cholesterol levels by several mechanisms, including blocking the formation of cholesterol in the liver.

As used herein the term "polycosanols" includes polycosanols or a salt thereof, preferably having a solubility in water of less than about 30 mg/ml, less than about 20 mg/ml, less than about 10 mg/ml, or more preferably less than about 1 mg/ml.

The one or more polycosanol particles, or salt thereof, can be in a crystalline phase, an amorphous phase, a semi-crystalline phase, a semi-amorphous phase, or a mixture thereof.

High LDL cholesterol is usually first treated with exercise, weight loss in obese individuals, and a diet low in cholesterol and saturated fats. When these measures fail, cholesterol-lowering medications, such as a polycosanol, can be added. The National Cholesterol Education Program (NCEP) has published treatment guidelines for use of polycosanols. These treatment guidelines take into account the level of LDL cholesterol as well as the presence of other risk factors such as diabetes, hypertension, cigarette smoking, low HDL cholesterol level, and family history of early coronary heart disease.

B. Surface Stabilizers

Surface stabilizers especially useful herein physically adhere on or associate with the surface of the nanoparticulate polycosanol but do not chemically react with the polycosanol particles or itself. Preferably, individual molecules of the surface stabilizer are essentially free of intermolecular cross-linkages.

The choice of a surface stabilizer for a polycosanol is non-trivial and required extensive experimentation to realize a desirable formulation for the active ingredient's therapeutic effect desired. For example, the effectiveness of using of a particular stabilizer with an active ingredient is unpredictable because the stabilizer among other factors, will affect dissolution and pharmacokinetic profiles for a polycosanol. Accordingly, the present invention is directed to the surprising discovery that stable, therapeutically useful, nanoparticulate polycosanol compositions can be made.

Combinations of more than one surface stabilizer can preferably be used in the invention. Useful surface stabilizers which can be employed in the invention include, but are not limited to, known organic and inorganic pharmaceutical excipients. Such excipients include various polymers, low molecular weight oligomers, natural products, and surfactants. Preferred surface stabilizers include nonionic, anionic, cationic, and zwitterionic surfactants.

Representative examples of surface stabilizers include hydroxypropylmethylcellulose (anionic), hydroxypropylcellulose, polyvinylpyrrolidone, sodium lauryl sulfate, dioctyl-sulfosuccinate (anionic), gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® stabilizers such as e.g., Tween 20® and Tween 80® stabilizers (ICI Speciality Chemicals)); polyethylene glycols (e.g., Carbowaxs 3550® and 934® (Union Carbide) polyethylene glycols), polyoxyethylene stearates, colloidal silicon dioxide, phosphates, carboxymethylcellulose calcium, carboxymethylcellulose sodium, methyl cellulose, hydroxyethylcellulose, hydroxypropylmethylcellulose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108® polyxamers, which are block copolymers of ethylene oxide and propylene oxide); poloxamines (e.g., Tetronic 908® poloxamine, also known as Poloxamine 908® poloxamine, which is a tetrafunctional block copolymer derived from sequential addition of propylene oxide and ethylene oxide to ethylenediamine (BASF Wyandotte Corporation, Parsippany, N.J.)); Tetronic 1508® (T-1508) stabilizer (BASF Wyandotte Corporation), Triton X-200® stabilizer, which is an alkyl aryl polyether sulfonate (Dow Chemical); Crodestas F-110® stabilizer, which is a mixture of sucrose stearate and sucrose distearate (Croda Inc.); p-isononylphenoxypoly-(glycidol), also known as Olin-10G® or Surfactant 10-G® stabilizer (Olin Chemicals, Stamford, Conn.); Crodestas SL-40® stabilizer (Croda, Inc.); and SA9OHCO stabilizer, which is $C_{18}H_{37}CH_2(-CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methyiglucamide; n-octyl-β-D-glucopyranoside; octyl β-D-thioglucopyranoside; PEG-derivatized phospholipid, PEG-derivatized cholesterol, PEG-derivatized cholesterol derivative, PEG-derivatized vitamin A, PEG-derivatized vitamin E, lysozyme, random copolymers of vinyl pyrrolidone and vinyl acetate, and the like such as Plasdone® S630 stabilizer in a 60:40 ratio of the pyrrolidone and vinyl acetate.

More examples of useful surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexadecyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$) dimethyl-benzyl ammonium chloride, N-tetradecylidmethyl-benzyl ammonium chloride monohydrate, dimethyl dodecylammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-dodecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), polyciuaternium 10 (POLYQUAT 10™), tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quatemized polyoxyethylalkylamines, MIRAPOL™ and ALKAQUAT™ (quartenized ammonium salt polymers, Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quatemary acrylamides; methylated quatemary polymers, such as poly[diallyl dimethylammonium chloride]and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric surface stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

The surface stabilizers are commercially available and/or can be prepared by techniques known in the art.

C. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients depending upon the route of administration and the dosage form desired. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 brand and Avicel®PH 102 brand, microcrystalline cellulose, and silicified microcrystalline cellulose (ProSolv SMCC™ brand).

Suitable lubricants, including agents that act on the flowability of the powder to be compressed, are colloidal silicon dioxide, such as Aerosil® brand, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® brand (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 brand and Avicel® PH102 brand; lactose such as lactose monohydrate, lactose anhydrous, and Pharmatose® DCL21 brand; dibasic calcium phosphate such as Emcompress® brand; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

D. Nanoparticulate Polycosanol Particle Size

The compositions of the invention contain polycosanol nanoparticles, such as sitosterol and/or phytosterol nanoparticles, which have an effective average particle size of less than about 2000 nm (i.e., 2 microns). In a preferred embodiment of the invention, the polycosanol nanoparticles have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than about 2000 nm" it is meant that at least 50% of the polycosanol particles have a particle size less than the effective average, by weight, i.e., less than about 2000 nm, about 1900 nm, about 1800 nm, etc., when measured by the above-noted techniques. Preferably, at least about 70%, about 90%, about 95%, or about 99% of the polycosanol particles have a particle size less than the effective average, i.e., less than about 2000 nm, about 1900 nm, about 1800 nm, etc.

In the present invention, the value for D50 of a nanoparticulate polycosanol composition is the particle size below which 50% of the polycosanol particles fall, by weight. Similarly, D90 is the particle size below which 90% of the polycosanol/stanol particles fall, by weight.

E. Concentration of Nanoparticulate Polycosanol and Surface Stabilizers

The relative amounts of at least one polycosanol and one or more surface stabilizers can vary widely. The optimal amount of the individual components depends, for example, upon one or more of the physical and chemical attributes of the particular polycosanol selected and surface stabilizer(s) selected, such as the hydrophilic lipophilic balance (HLB), melting point, and the surface tension of water solutions of the stabilizer, etc.

Preferably, the concentration of the at least one polycosanol can vary from about 99.5% to about 0.001%, preferably from about 95% to about 0.1%, preferably from about 90% to about 0.5%, by weight, based on the total combined weight of the polycosanol and at least one surface stabilizer, not including other excipients. Higher concentrations of the active ingredient are generally preferred from a dose and cost efficiency standpoint.

Preferably, the concentration of the at least one surface stabilizer can vary from about 0.5% to about 99.999%, from about 5.0% to about 99.9%, or from about 10% to about 99.5%, by weight, based on the total combined dry weight of the polycosanol and at least one surface stabilizer, not including other excipients.

Exemplary useful ratios of active ingredient to stabilizers herein are preferably about 1:1, preferably about 2:1, preferably about 3:1, preferably about 4:1, preferably about 5:1, preferably about 6:1, preferably about 7:1, preferably about 8:1, and preferably about 10:1, by weight, based on the total combined dry weight of the polycosanol and at least one surface stabilizer, not including other excipients.

III. Methods of Making Nanoparticulate Polycosanol Compositions

The nanoparticulate polycosanol compositions can be made using any suitable method known in the art such as, for example, milling, homogenization, or precipitation techniques. Exemplary methods of making nanoparticulate compositions are described in the '684 patent. Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

The resultant nanoparticulate polycosanol compositions or dispersions can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc. Solid dose forms of the dispersions of novel polycosanol formulations according to the present invention can be made as described in U.S. Pat. No. 6,375,986.

A. Milling to Obtain Nanoparticulate Polycosanol Dispersions

Milling a polycosanol to obtain a nanoparticulate polycosanol dispersion comprises dispersing polycosanol particles in a liquid dispersion medium in which the polycosanol is poorly soluble, followed by applying mechanical means in the presence of grinding media to reduce the particle size of the polycosanol to the desired effective average particle size. The dispersion medium can be, for example, water, safflower oil, ethanol, t-butanol, glycerin, polyethylene glycol (PEG), hexane, or glycol.

The polycosanol particles can be reduced in size preferably in the presence of at least one surface stabilizer. Alternatively, the polycosanol particles can be contacted with one or more surface stabilizers after attrition. Other compounds, such as a diluent, can be added to the polycosanol/surface stabilizer composition during the size reduction process. Dispersions can be manufactured continuously or in a batch mode.

B. Precipitation to Obtain Nanoparticulate Polycosanol Compositions

Another method of forming the desired nanoparticulate polycosanol composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving a polycosanol in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by conventional means.

C. Homogenization to Obtain Polycosanol Nanoparticulate Compositions

Exemplary homogenization methods of preparing active agent nanoparticulate compositions are described in U.S. Pat. No. 5,510,118, for "Process of Preparing Therapeutic Compositions Containing Nanoparticles." Such a method comprises dispersing polycosanol particles in a liquid dispersion medium in which the polycosanol is poorly soluble, followed by subjecting the dispersion to homogenization to reduce the particle size of the polycosanol to the desired effective average particle size. The polycosanol particles are preferably reduced in size in the presence of at least one surface stabilizer. Alternatively, the polycosanol particles can be contacted with one or more surface stabilizers either before or after attrition. Other compounds, such as a diluent, can be added to the polycosanol/surface stabilizer composition before, during, or after the size reduction process. Dispersions can be manufactured continuously or in a batch mode.

IV. Methods of Using Polycosanol Compositions of the Current Invention

The polycosanol compositions of the present invention can be administered to a subject via any conventional means including, but not limited to, preferably orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms patient and subject may be used interchangeably.

The present invention provides a method of prolonging plasma levels of a polycosanol in a subject while achieving the desired therapeutic effect. In one aspect, such a method comprises orally administering to a subject an effective amount of a composition of this invention comprising a polycosanol.

In one aspect, the compositions of the invention are useful in treating conditions that may be directly or indirectly associated with elevated and/or uncontrolled cholesterol metabolism as described herein and known to those in the art.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate polycosanol compositions may also contain adjuvants such as preserving, wetting, emulsifying, and dispensing agents. Prevention of the growth of microorganisms can also be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration are preferred and include, but are not limited to, capsules, tablets, pills, powders, caplets, and granules. In such solid dosage forms, the active agent (i.e., the composition of this invention) is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable dispersions, emulsions, solutions, suspensions, syrups, and elixirs. In addition to the active agent, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

The effective amounts of the polycosanol compositions of the invention can be determined empirically and can be employed in pure form or, where such forms exist, in pharmaceutically acceptable salt, ester, or prodrug form. Actual dosage levels of polycosanol in the nanoparticulate compositions of the invention may be varied to obtain an amount of polycosanol that is effective to obtain a desired therapeutic response for a particular composition, method of administration, and the condition to be treated. The selected dosage level therefore depends upon the desired therapeutic effect, the route of administration, the potency of the administered polycosanol, the desired duration of treatment, and other factors.

Dosage unit compositions may contain amounts of submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration and rate of excretion of the agent; the duration of the treatment; drugs used in combination or coincidental with the specific agent; and like factors well known in the medical arts.

V. Polycosanol Combinations

Polycosanol compositions of the present invention are also particularly useful when given pursuant to the method of this invention in combination with a therapeutically effective amount of at least one other non-polycosanol active agent useful: (1) in treating conditions such as dyslipidemia, hyperlipidemia, hypercholesterolemia, cardiovascular disorders, hypertriglyceridemia, coronary heart disease, and peripheral vascular disease (including symptomatic carotid artery disease), or related conditions; (2) as adjunctive therapy to diet for the reduction of LDL-C, total-C, triglycerides, and/or Apo B in adult patients with primary hypercholesterolemia or mixed dyslipidemia (Fredrickson Types IIa and IIb); (3) as adjunctive therapy to diet for treatment of adult patients with hypertriglyceridemia (Fredrickson Types IV and V hyperlipidemia); (4) in treating pancreatitis; (5) in treating restenosis; and/or (6) in treating Alzheimer's disease.

Exemplary non-polycosanol compositions useful in the invention include, e.g., cholesterol lowering agents, alkanoyl L-carnitines, antihypertensives, statins, sterols, and/or stanols.

Useful cholesterol lowering agents are well known to those of skill in the art and include, but are not limited to, ACE inhibitors, nicotinic acid, niacin, bile acid sequestrants, fibrates, vitamins, fatty acid derivatives such as fish oil, long chain plant extract alcohols such as policosinol, ezetimibe, and celluloses.

Useful alkanoyl L-carnitines include, but are not limited to, acetyl L-carnitine, propionyl L-carnitine, butyryl L-carnitine, valeryl L-carnitine, and isovaleryl L-carnitine, or a pharmacologically acceptable salt thereof.

Useful antihypertensives include, but are not limited to diuretics ("water pills"), beta blockers, alpha blockers, alpha-beta blockers, sympathetic nerve inhibitors, angiotensin converting enzyme (ACE) inhibitors, calcium channel blockers, angiotensin receptor blockers (formal medical name angiotensin-2-receptor antagonists, known as "sartans" for short).

Useful statins include, but are not limited to, atorvastatin (Lipitort® brand) (U.S. Pat. No. 4,681,893) and other 6-[2-(substituted-pyrrol-1-yl)alkyl]pyran-2-ones and derivatives as disclosed in U.S. Pat. No. 4,647,576); fluvastatin (Lescol® brand) (U.S. Pat. No. 5,354,772); lovastatin (U.S. Pat. No. 4,231,938); pravastatin (U.S. Pat. No. 4,346,227); simvastatin (U.S. Pat. No. 4,444,784); velostatin; fluindostatin (Sandoz XU-62-320); pyrazole analogs of mevalonolactone derivatives, as disclosed in PCT application WO 86/03488; rivastatin and other pyridyldihydroxyheptenoic acids, as disclosed in European Patent 491226A; Searle's SC-45355 (a 3-substituted pentanedioic acid derivative); dichloroacetate; imidazole analogs of mevalonolactone, as disclosed in PCT application WO 86/07054; 3-carboxy-2-hydroxy-propane phosphonic acid derivatives, as disclosed in French Patent No. 2,596,393; 2,3-di-substituted pyrrole, furan, and thiophene derivatives, as disclosed in European Patent Application No. 0221025; naphthyl analogs of mevalonolactone, as disclosed in U.S. Pat. No. 4,686,237; octahydronaphthalenes, such as those disclosed in U.S. Pat. No. 4,499,289; keto analogs of mevinolin (lovastatin), as disclosed in European patent application No. 0,142,146 A2; phosphinic acid compounds; as well as other HMG CoA reductase inhibitors.

Useful sterols and/or stanols include, but are not limited to, plant sterols, plant sterol esters, fish oil, sitosterol, sitostanol, phytosterol, campestanol, stigmasterol, coprostanol, cholestanol, and beta-sitosterol.

The term "stanol" is well known to those skilled in the art and generally refers to compounds having a saturated perhydrocyclopentanophenanthrene ring system and having one or more OH substituents. "Stanols" as used herein mean plant stanol esters, a food ingredient that can help reduce LDL cholesterol. Plant stanols are derived from naturally occurring substances in plants by techniques known to those in the art.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

In the examples that follow, the particle sizes were measured using a Horiba LA-910 Laser Scattering Particle Size Distribution Analyzer (Horiba Instruments, Irvine, Calif.). The particle mean and $D_{90}$ (which is the size below which 90% of the distribution is located) are obtained from a weight distribution. All formulations are given in weight % (w/w).

EXAMPLE 1

The purpose of this example was to identify formulations that would produce stable nanoparticulate dispersions of polycosanol.

Arriving at a formulation that results in a stable dispersion having a small particle size is nontrivial and requires extensive experimentation.

Two grades of polycosanol were evaluated, labeled OCTA-60 (Formulation A) and OCTA-95 (Formulation B). The 1-octacosanol content is ca 60% in Formulation A and ca 95% in Formulation B. Both contain a total of ca 97 to 98% long chain aliphatic alcohols, such as 1-octacosanol, 1-triacontanol, 1-dotriactontanol, 1-hexacosanol, and 1-heptacosanol.

The polycosanol was commercially obtained from Garuda International, Lemon Cove, Calif. and the specifications for each product used herein are available from the company's web site.

Formulation A, comprising 5% (w/w) polycosanol OCTA-60 and 1% (w/w) Tween® 80 stabilizer, and Formulation B, comprising 5% (w/w) polycosanol OCTA-95 and 1% (w/w) Tween® 80stabilizer, were each processed in a DYNO®-Mill KDL type mill (Willy A. Bachofen A G, Maschinenfabrik, Basel, Switzerland) equipped with a 150 cc batch chamber using a 500 µm milling media of type Polymill® 500 for 6.5-7 hrs at 10° C.

The polycosanol particle sizes for Formulations A and B were measured using a Horiba LA-910 Laser Scattering Particle Size Distribution Analyzer (Horiba Instruments, Irvine, Calif.). The polycosanol particle mean and $D_{90}$ were obtained from a weight distribution. The results are shown in Table 2, below.

TABLE 1

| Active ingredient | Stabilizer | Size at harvest | | Size after 2 weeks at 25° C. | | 1 min sonication |
|---|---|---|---|---|---|---|
| | | Mean (nm) | D90 (nm) | Mean (nm) | D90 (nm) | |
| A. 5% Polycosanol OCTA-60 | 1.0% Tween ® 80 (Polysorbate 80) | 292,000 | 579,000 | 710 | 998 | N |
| | | 317 | 496 | 317 | 998 | Y |
| B. 5% Polycosanol OCTA-95 | 1.0% Tween ® 80 (Polysorbate 80) | 240 | 368 | 245 | 385 | N |
| | | 236 | 362 | 221 | 342 | Y |

The results show that the product of higher purity, OCTA-95, produces a more stable dispersion as indicated by the size before and after sonication. It should be noted, however, that while the OCTA-60 formulation initially seems prone to aggregation, it relaxes into a more stable dispersion upon aging. Thus, both types of polycosanol are suitable for the nanoparticulate polycosanol compositions of the invention.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A stable pharmaceutical composition comprising:
   (a) a therapeutically effective amount of particles of at least one polycosanol or a salt thereof which comprise 55 to 70% octacosanol or an octacosanol content of OCTA-95 (approximately 80-95% octacosanol), wherein the polycosanol particles have an effective average particle size of less than 1000 nm; and
   (b) at least one polyoxyethylene sorbitan fatty acid ester surface stabilizer;
   said composition having a dissolution profile wherein within about 5 minutes at least 20% of the composition is dissolved.

2. The composition of claim 1, wherein the particles comprise about 55-70% octacosanol.

3. The composition of claim 1, wherein the polycosanol particles are in a phase selected from the group consisting of a crystalline phase, an amorphous phase, a semi-crystalline phase, and mixtures thereof.

4. The composition of claim 1, wherein the effective average particle size of the polycosanol particles is selected from the group consisting of less than 1000 nm, less than 900 nm, less than 800 nm, less than 700 nm, less than 600 nm, less than 500 nm, less than 400 nm, less than 300 nm, less than 250 nm, less than 200 nm, less than 100 nm, less than 75 nm, and less than 50 nm.

5. The composition of claim 1, wherein the composition is formulated for administration selected from the group consisting of oral, pulmonary, rectal, opthalmic, colonic, parenteral, intracisternal, intravaginal, intraperitoneal, local, buccal, nasal, and topical administration.

6. The composition of claim 1 formulated into a dosage form selected from the group consisting of liquid dispersions, oral suspensions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations.

7. The composition of claim 1, wherein the composition further comprises one or more pharmaceutically acceptable excipients, carriers, or a combination thereof.

8. The composition of claim 1, wherein the at least one polycosanol or a salt thereof is present in an amount from about 90% to about 0.5%, by weight, based on the total combined weight of the polycosanol or a salt thereof and at least one surface stabilizer, not including other excipients.

9. The composition of claim 1, wherein the at least one surface stabilizer is present in an amount from about 10% to about 99.5% by weight, based on the total combined dry weight of the polycosanol or a salt thereof and at least one surface stabilizer, not including other excipients.

10. The composition of claim 1, further comprising at least one secondary surface stabilizer.

11. The composition of claim 1 further comprising a surface stabilizer selected from the group consisting of an anionic surface stabilizer, a cationic surface stabilizer, a zwitterionic surface stabilizer, and a non-ionic surface stabilizer.

12. The composition of claim 11, wherein the surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, castor oil, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-phospholipid, PEG-cholesterol, PEG-cholesterol, PEG-vitamin A, and random copolymers of vinyl acetate and vinyl pyrrolidone.

13. The composition of claim 11, wherein the cationic surface stabilizer is selected from the group consisting of a polymer, a biopolymer, a polysaccharide, a cellulosic, an alginate, a nonpolymeric compound, and a phospholipid.

14. The composition of claim 11, wherein the surface stabilizer is selected from the group consisting of cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quartemary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl $(C_{12-18})$dimethylbenzyl ammonium chloride, N-alkyl $(C_{14-18})$dimethyl-benzyl ammonium chloride, N-tetradecylidmethylbenzyl ammonium chloride monohydrate, dimethyl dodecyl ammonium chloride, N-alkyl and $(C_{12-14})$ dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-dodecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10 stabilizer, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts; amines, amine salts, amine oxides, imide azolinium salts, protonated quaternary acrylamides, methylated quaternary polymers, and cationic guar.

15. The composition of any of claims 11, 13, or 14, wherein the composition is bioadhesive.

16. The composition of claim 1, comprising Tween® 80 stabilizer as a surface stabilizer.

17. The composition of claim 1, wherein the $T_{max}$ of the polycosanol, when assayed in the plasma of a mammalian subject following administration, is less than the $T_{max}$ for a conventional, non-nanoparticulate form of the same polycosanol, administered at the same dosage.

18. The composition of claim 17, wherein the $T_{max}$ of the polycosanol is not greater than 50% of the $T_{max}$ exhibited by a non-nanoparticulate formulation of the same polycosanol, administered at the same dosage.

19. The composition of claim 1, wherein the $C_{max}$ of the polycosanol, when assayed in the plasma of a mammalian subject following administration, is greater than the $C_{max}$ for a conventional, non-nanoparticulate form of the same polycosanol, administered at the same dosage.

20. The composition of claim 19, wherein the $C_{max}$ of the polycosanol is greater than the $C_{max}$ exhibited by a non-nanoparticulate formulation of the same polycosanol, administered at the same dosage.

21. The composition of claim 1, wherein the AUC of the polycosanol, when assayed in the plasma of a mammalian subject following administration, is greater than the AUC for a conventional, non-nanoparticulate form of the same polycosanol, administered at the same dosage.

22. The composition of claim 21, wherein the AUC of the polycosanol is greater than the AUC exhibited by a non-nanoparticulate formulation of the same polycosanol, administered at the same dosage.

23. The composition of claim 1 which does not produce significantly different absorption levels when administered under fed as compared to fasting conditions.

24. The composition of claim 23, wherein the difference in absorption of the polycosanol composition of the invention, when administered in the fed versus the fasted state, is less than 50%.

25. The composition of claim 1, wherein administration of the composition to a subject in a fasted state is bioequivalent to administration of the composition to a subject in a fed state, when administered to a human.

26. The composition of claim 25, wherein "bioequivalency" is established by a 90% Confidence Interval of between 0.80 and 1.25 for both $C_{max}$ and AUC, when administered to a human.

27. The composition of claim 25, wherein "bioequivalency" is established by a 90% Confidence Interval of between 0.80 and 1.25 for AUC and a 90% Confidence Interval of between 0.70 to 1.43 for $C_{max}$, when administered to a human.

28. The composition of claim 1, wherein within about 5 minutes at least 20% of the composition is dissolved, wherein dissolution is measured in a media which is discriminating and wherein the rotating blade method (European Pharmacopoeia) is used to measure dissolution.

29. The composition of claim 28, in which at least 30% of the composition is dissolved within about 5 minutes.

30. The composition of claim 28, wherein upon redispersion the polycosanol particles have an effective average particle size of less than 2 microns.

31. The composition of claim 1, wherein within about 10 minutes at least 40% of the composition is dissolved, wherein dissolution is measured in a media which is discriminating and wherein the rotating blade method (European Pharmacopoeia) is used to measure dissolution.

32. The composition of claim 31, wherein at least 50% of the composition is dissolved within about 10 minutes.

33. The composition of claim 31, wherein upon redispersion the polycosanol particles have an effective average particle size of less than 2 microns.

34. The composition of claim 1, wherein within about 20 minutes at least 70% of the composition is dissolved, wherein dissolution is measured in a media which is discriminating and wherein the rotating blade method (European Pharmacopoeia) is used to measure dissolution.

35. The composition of claim 34, wherein at least 90% of the composition is dissolved within about 20 minutes.

36. The composition of claim 34, wherein upon redispersion the polycosanol particles have an effective average particle size of less than 2 microns.

37. The composition of claim 1, additionally comprising one or more non-polycosanol active agents selected from the group consisting of:
  (a) an active agent useful in treating dyslipidemia;
  (b) an active agent useful in treating hyperlipidemia;
  (c) an active agent useful in treating hypercholesterolemia;
  (d) an active agent useful in treating cardiovascular disorders;
  (e) an active agent useful in treating hypertriglyceridemia;
  (f) an active agent useful in treating coronary heart disease;
  (g) an active agent useful in treating peripheral vascular disease;
  (h) an active agent useful as adjunctive therapy to diet for the reduction of LDL-C, total-C, triglycerides, and/or Apo B in adult patients with primary hypercholesterolemia or mixed dyslipidemia (Fredrickson Types IIa and IIb);
  (i) an active agent useful as adjunctive therapy to diet for treatment of adult patients with hypertriglyceridemia (Fredrickson Types IV and V hyperlipidemia);
  (j) an active agent useful in treating pancreatitis;
  (k) an active agent useful in treating restenosis; and
  (l) an active agent useful in treating Alzheimer's disease.

38. The composition of claim 1, additionally comprising one or more non-polycosanol active agents selected from the group consisting of cholesterol lowering agents, alkanoyl L-carnitines, antihypertensives, statins, sterols, and stanols.

39. The composition of claim 38, wherein the cholesterol lowering agent is selected from the group consisting of ACE inhibitors, nicotinic acid, niacin, bile acid sequestrants, fibrates, vitamins, fatty acid derivatives, long chain plant extract alcohols, ezetimibe, and celluloses.

40. The composition of claim 38, wherein the antihypertensive is selected from the group consisting of diuretics, beta blockers, alpha blockers, alpha-beta blockers, sympathetic nerve inhibitors, angiotensin converting enzyme (ACE) inhibitors, calcium channel blockers, and angiotensin receptor blockers.

41. The composition of claim 38, wherein the statin is selected from the group consisting of atorvastatin; a 6-[2-(substituted-pyrrol-1-yl)alkyl]pyran-2-ones and derivative other than atorvastatin; lovastatin; a keto analog of mevinolin other than lovastatin; pravastatin; simvastatin; velostatin; fluindostatin; pyrazole analogs of mevalonolactone derivatives; rivastatin; a pyridyldihydroxyheptenoic acid other than rivastatin; SC-45355; dichloroacetate; imidazole analogs of mevalonolactone; 3-carboxy-2-hydroxy-propane- phosphonic acid derivatives; 2,3-di-substituted pyrrole derivatives; 2,3-di-substituted furan derivatives; 2,3-di-substituted thiophene derivatives; naphthyl analogs of mevalonolactone; octahydronaphthalenes; and phosphinic acid compounds.

42. The composition of claim 38, wherein the sterol or stanol is selected from the group consisting of plant sterols, plant sterol esters, fish oil, sitosterol, sitostanol, phytosterol, campestanol, stigmasterol, coprostanol, cholestanol, and beta-sitosterol.

43. The composition according to claim 37 or 38, wherein at least one of the non-polycosanol compounds has an effective average particle size of greater than 2 microns.

44. The composition according to claim 37 or 38, wherein at least one of the non-polycosanol compounds has an effective average particle size of less than 2 microns.

45. The composition of claim 1, wherein upon administration the composition redisperses such that the polycosanol particles have an effective average particle size of less than 1000 nm.

46. The composition of claim 1, wherein the composition redisperses in a biorelevant media such that the polycosanol particles have an effective average particle size of less than 1000 nm.

47. A method of making a stable polycosanol composition comprising contacting a therapeutically effective amount of particles of at least one polycosanol or a salt thereof which comprise 55% to 70% octacosanol or an octacosanol content of OCTA-95 (approximately 80-95% octacosanol), with at least one polyoxyethylene sorbitan fatty acid ester surface stabilizer for a time and under conditions sufficient to provide a stable polycosanol composition having an effective average particle size of less than 1000 nm and having a dissolution profile wherein within about 5 minutes at least 20% of the composition is dissolved.

48. The method of claim 47, wherein said contacting comprises grinding.

49. The method of claim 48, wherein said grinding comprises wet grinding.

50. The method of claim 47, wherein said contacting comprises homogenizing.

51. The method of claim 47, wherein said contacting comprises:
(a) dissolving the particles of a polycosanol or a salt thereof in a solvent;
(b) adding the resulting polycosanol solution to a solution comprising at least one surface stabilizer; and
(c) precipitating the solubilized polycosanol having at least one surface stabilizer adsorbed on the surface thereof by the addition thereto of a non-solvent.

52. The method of claim 47, wherein the particles comprise 55-70% octacosanol.

53. The method of claim 47, wherein the polycosanol particles are in a phase selected from the group consisting of a crystalline phase, an amorphous phase, a semi-crystalline phase, and mixtures thereof.

54. The method of claim 47, wherein the composition is formulated for administration selected from the group consisting of oral, pulmonary, rectal, opthalmic, colonic, parenteral, intracisternal, intravaginal, intraperitoneal, local, buccal, nasal, and topical administration.

55. The method of claim 47, wherein the composition further comprises one or more pharmaceutically acceptable excipients, carriers, or a combination thereof.

56. The method of claim 47, wherein the polycosanol or a salt thereof is present in an amount from about 90% to about 0.5%, by weight, based on the total combined weight of the polycosanol or a salt thereof and at least one surface stabilizer, not including other excipients.

57. The method of claim 47, wherein the at least one surface stabilizer is present in an amount selected from about 10% to about 99.5% by weight, based on the total combined dry weight of the polycosanol or a salt thereof and at least one surface stabilizer, not including other excipients.

58. The method of claim 47, further comprising contacting the particles with at least one secondary surface stabilizer.

59. The method of claim 58, wherein the surface stabilizer is selected from the group consisting of an anionic surface stabilizer, a cationic surface stabilizer, a zwitterionic surface stabilizer, and a non-ionic surface stabilizer.

60. The method of claim 59, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, castor oil, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-phospholipid, PEG-cholesterol, PEG-cholesterol, PEG-vitamin A, PEG-vitamin E, and random copolymers of vinyl acetate and vinyl pyrrolidone.

61. The method of claim 59, wherein the at least one cationic surface stabilizer is selected from the group consisting of a polymer, a biopolymer, a polysaccharide, a cellulosic, an alginate, a nonpolymeric compound, and a phospholipid.

62. The method of claim 59, wherein the surface stabilizer is selected from the group consisting of cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quartemary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl dodecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-dodecyl dimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethylammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquatemium 10 stabilizer, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quarternized ammonium salt polymers, alkyl pyridinium salts; amines, amine salts, amine oxides, imide azolinium salts, protonated quaternary acrylamides, methylated quaternary polymers, and cationic guar.

63. The method of any of claims 59, 61, or 62, wherein the composition is bioadhesive.

64. The method of claim 47, comprising Tween® 80 stabilizer as a surface stabilizer.

65. The composition of claim 1, wherein the particles comprise the ocatacosanol content of OCTA-95 (approximately 80-95% octacosanol).

66. The composition of claim 1, wherein the particles comprise approximately 95% octacosanol.

* * * * *